(12) United States Patent
Nacson

(10) Patent No.: US 9,063,100 B2
(45) Date of Patent: Jun. 23, 2015

(54) TRANSPORTABLE PORTAL FOR DETECTION OF ILLICIT SUBSTANCES

(75) Inventor: Sabatino Nacson, Thornhill (CA)

(73) Assignee: TeknoScan Systems Inc., Vaughan, Ontario (CA)

( * ) Notice: Subject to any disclaimer, the term of this patent is extended or adjusted under 35 U.S.C. 154(b) by 35 days.

(21) Appl. No.: 13/284,406

(22) Filed: Oct. 28, 2011

(65) Prior Publication Data

US 2012/0103061 A1 May 3, 2012

Related U.S. Application Data

(60) Provisional application No. 61/407,506, filed on Oct. 28, 2010.

(51) Int. Cl.
*G01N 33/00* (2006.01)
*G01N 30/02* (2006.01)

(52) U.S. Cl.
CPC ...... *G01N 33/0004* (2013.01); *G01N 2030/025* (2013.01)

(58) Field of Classification Search
CPC .................................................. G01N 33/0004
See application file for complete search history.

(56) References Cited

U.S. PATENT DOCUMENTS

| 4,045,997 | A | * | 9/1977 | Showalter et al. ............. 73/23.2 |
| 4,987,767 | A | * | 1/1991 | Corrigan et al. ............. 73/23.36 |
| 5,753,832 | A | * | 5/1998 | Bromberg et al. ......... 73/864.81 |
| 5,915,268 | A | * | 6/1999 | Linker et al. ................... 73/23.2 |
| 2010/0067014 | A1 | * | 3/2010 | Howieson ..................... 356/437 |
| 2010/0213365 | A1 | * | 8/2010 | Crowley et al. .............. 250/282 |

* cited by examiner

*Primary Examiner* — Laura Martin
*Assistant Examiner* — Alex Devito
(74) *Attorney, Agent, or Firm* — Kagan Binder, PLLC

(57) ABSTRACT

The present invention is a transportable portal for screening a target, which may be a person, standing or placed inside the portal. It employs two walls with air ducts in the walls, usually two ducts per wall running from the bottom to the top of each wall, and having a number of air intakes spaced along the height of the wall. A blower module blows air downward on the target to dislodge particles and vapor, which are drawn in the air ducts and analyzed by a detection module. Each detection module may have a pre-concentrator with a nano-platinum surface for collecting and pyrolyzing samples, and chemical, optical and radiation detectors for detecting illicit materials. The portal may be disassembled or reassembled by two people using hand tools in less than one hour and then placed in a space of less than one cubic meter for transport.

24 Claims, 6 Drawing Sheets

TRANSPORTABLE PORTAL FOR DETECTION OF ILLICIT SUBSTANCES

PRIORITY CLAIM

This application claims the benefit of U.S. Provisional Application Ser. No. 61/407,506 filed Oct. 28, 2010, entitled TRANSPORTABLE PORTAL FOR DETECTING OF ILLICIT SUBSTANCES, the disclosure of which is incorporated herein by reference.

FIELD OF THE INVENTION

The present invention relates generally to screening persons, luggage and other items, and in particular, to a non-invasive transportable apparatus for detecting the presence of illicit substances on a target.

BACKGROUND OF THE INVENTION

It is common practice to screen targets, including people, freight, luggage and other items, to detect the presence of illicit substances. Illicit substances include, for example, narcotics, explosives, chemical warfare agents, biological warfare agents, nuclear or radiological agents, toxic industrial chemicals or waste, and controlled or contraband items such as tobacco.

The presence of explosives on a person's body, clothing and hair can be detected by sensing microscopic particles located on the person or vapors emitted from concealed threat materials on the person's clothes. To detect illicit substances, various techniques may be used, such as physical search, identifying anomalies on a person's body by detecting changes in the dielectric constant within a defined space, and electromagnetic imaging using technologies such as x-ray back scatter, millimeter-wave, or low-power microwave.

Some techniques offers a high probability of identifying presence of explosives, such as physical search, but suffer from being invasive and time-consuming. Others offer lower probability of detection and may be too revealing when applied to a person, raising the issue of invasion of privacy.

Existing trace chemical detection portals (TCDPs) sample the air surrounding a person who is inside the portal, collecting dislodged particulate matter on a single pre-concentrator (usually a large diameter mesh) at high flowrate. The mesh is heated to vaporize the sample into a secondary mesh or directly into an analyzer. The analyzer is usually an ion mobility spectrometer or a more sophisticated quadrupole ion trap, time-of-flight mass analyzer.

TCDPs may be open design or closed door design. In both approaches, fans in the ceiling typically blow downward over the body of a person inside the portal and air jets in the sidewalls provide agitation to remove particulate matter from the person. Explosive vapor and particles are transported in the downward airflow to an exhaust slot near the floor and then through a two-stage pre-concentrator. This design is used in multiple commercially available portals. In another approach, the air is moved upward, relying on the temperature of the human body to generate a convection plume, which causes vapor around the body to move upward to a collection system.

Other designs employ a tunnel that a person walks through and which samples the air carrying any dislodged particulate matter and, vapor while the person walks through the tunnel. Ceiling fans may pull the air upward towards pre-concentrator tubes and into a fast gas chromatography (GC)-electron capture detector.

Because existing designs use a single pre-concentration and analysis module that handles all samples of air ingested by the exhaust slot, including debris such as hairs, they suffer from various problems. The collection of debris, hairs, fibers, and dust eventually saturates the primary mesh of the single large pre-concentrator, reducing sensitivity to explosives and other illicit substances, and introducing major contamination to the analysis system. This results in the requirement for frequent cleaning of the meshes and ducts, and results in the systems working sub-optimally much of the time. In some systems, periodic replacement of the pre-concentrator mesh assembly is required, making field repair costly and laborious.

The need for powerful compressors and blowers to drive particles though the interior to the exhaust slot and the use of a large single centralized pre-concentrator and detection modules results in bulky portals are very difficult to transport between facilities and relocate within a facility.

They also require a large amount of power for their compressors and blowers and have specialized installation and power requirements. They employ heavy and bulky compressors to generate the air jets, and typically use a large blower cable of blowing over 20,000 liters per minute. The noise generated by the compressors and blowers also results in the need for noise reduction measures to be taken in the design, which adds to the bulk and cost of the units.

SUMMARY OF THE INVENTION

The invention is directed to a portal for screening a target that includes a person, the portal comprising:
   a. a frame defining an interior region for accommodating the target, the frame having at least one air duct for receiving air from the interior region;
   b. a blower module for directing a flow of air at the target in the interior region to dislodge particles and vapor on or surrounding the target, wherein the air flow carries the dislodged particles and vapor away from the target;
   c. at least one duct air intake in each air duct for receiving air carrying particles and vapor from the interior region at a plurality of intake points at a plurality of heights along the body of the person located in the interior region; and
   d. a detection module in pneumatic communication with each air duct for sampling and processing air in the air ducts, the detection module comprising a pre-concentrator module for collecting and pre-concentrating the particles and vapor from the air, and a chemical sensor for detecting illicit substances by chemically analyzing the pre-concentrated particles and vapor.

The interior region may be at least six feet high and the highest intake point may be at least three feet higher than the lowest intake point. The lowest intake point may be at most three feet above the feet of a person standing in the interior region. The highest intake point may be at least four feet higher than the lowest intake point and the lowest intake point may be at most two feet above the feet of a person standing in the interior region.

Each air duct may have at least six duct air intakes for receiving air from six different heights.

The pre-concentrator module may pyrolyze particles and vapor.

The portal may be designed so that it can be disassembled or reassembled by two people using hand tools in less than one hour.

The portal may be open on opposite sides to allow people to enter and exit the portal easily.

The portal may have at least two detection modules.

The frame may include two walls, each wall having at least one air duct therethrough.

Each wall may have two air ducts extending to the top of the walls and the portal may also have a pneumatic system for drawing the air carrying particles and vapor through the air ducts towards the tops of the walls.

A separate detection module may be in pneumatic communication with each air duct.

The portal may have a manifold for receiving air carrying particles and vapor from the air ducts and directing the air to the air intake of the air curtain module for recirculation of the air. The portal may be configurable to prevent recirculation of the air.

The portal may include a fan in each wall located near the bottom of the wall.

The air curtain module may be able to produce air flow at a velocity of at least 10 meters per second and the velocity of the air flow may be adjustable.

The air curtain module may include a heater to heat incoming air to a temperature above room temperature.

The portal may include a camera for talking a photograph of the target when an illicit substance is detected.

The target may be a person and the walls may be at least six feet high.

Each wall may have at least two rigid portions, the portions being foldably attached to each other for folding the wall to reduce its spatial extent.

The portal may be designed so that it can be disassembled and the walls folded so that the disassembled portal fits in a space that is less than 1.5 cubic meters in volume, or less than 1.0 cubic meter.

The portal may weigh less than 200 kilograms, and may weigh less than 150 kilograms.

The detection module may include an optical sensor and may also include a radiation sensor for detecting beta, gamma and alpha radioactivity.

The portal may have a processor for receiving analysis results from the detection module and generating illicit substance information.

The pre-concentrator module may be a miniature pre-concentrator comprising a surface coated with platinum nano-dendrites. The pre-concentrator module may have more than one collection surface and the pyrolysis may be performed by heating the collection surfaces to different temperatures. For example, pre-concentrator module may have four collection surfaces.

The chemical sensor may be, for example, an ion mobility spectrometer, a differential mobility spectrometer, or a mass analyzer system. The chemical sensor may include a fast gas chromatography system interfaced to an electron-capture detector.

The portal may have wheels for moving the portal along a surface.

DETAILED DESCRIPTION

Figure 1:
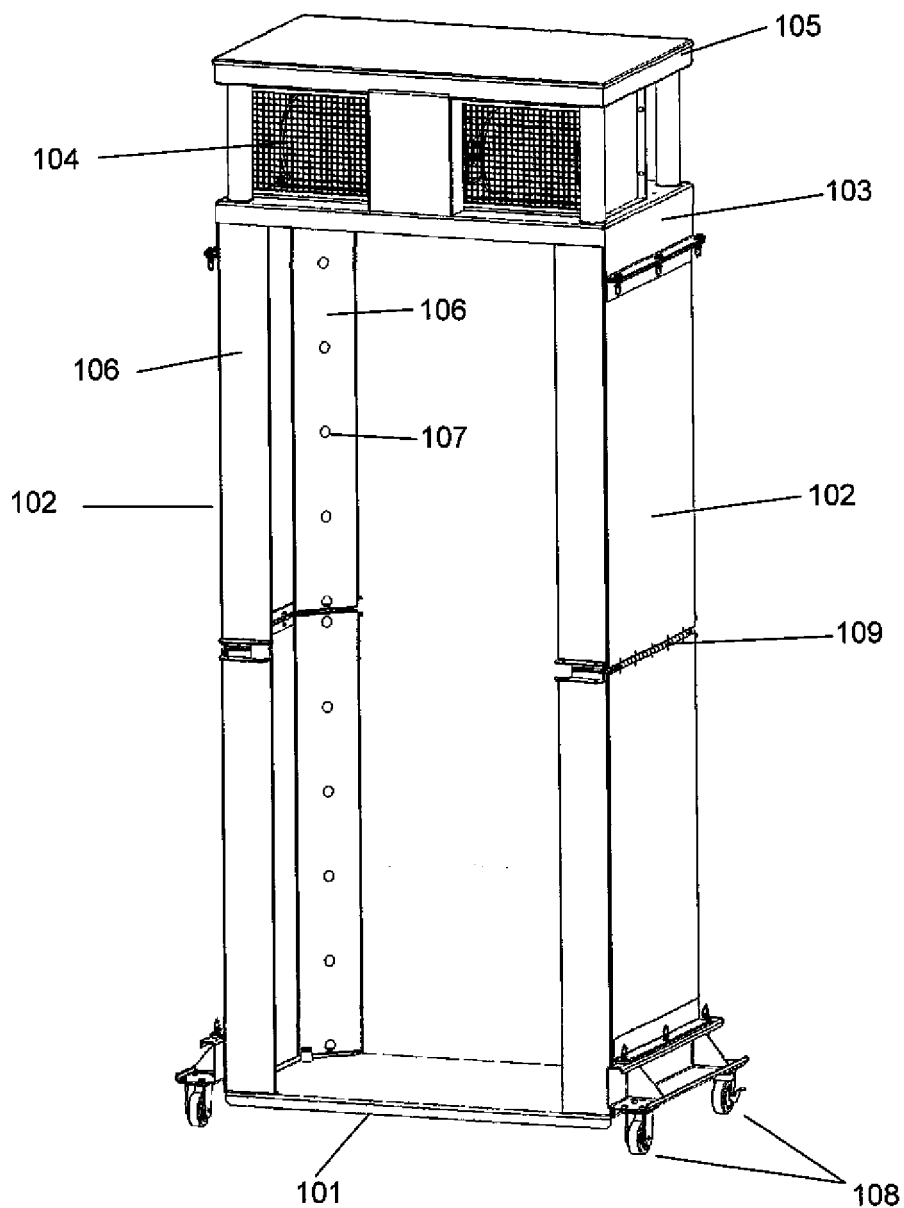
FIG. 1 is a perspective view of an embodiment of the invention.

One embodiment of the invention is shown in FIG. 1. The figure shows 6 modules: a base 101, two walls 102, a top plate 103, a blower module 104, and a recirculating manifold 105. The base 101, walls 102, and top plate 103 constitute a frame that defines an interior region between the walls 102. The components may be better seen in FIG. 2, which provides an exploded view of the same embodiment.

The top plate 103 and manifold 105 are not essential. For example, the blower module 104 could be mounted directly on the tops of the walls 102, and the manifold 105 is optional. It is only necessary that the frame define an interior region that is sufficient to accommodate a person, which generally means that the interior region is at least six feet, and preferably at least 80 inches, high, and have a width and depth sufficient for a person standing in the interior region, which could be, for example, 30 inches wide and 24 inches deep. In the embodiment shown in FIG. 1, the walls are about 30 inches apart, and the base and top plate are about 24 inches wide, which defines the depth of the interior region.

In the embodiment shown in FIG. 1, the walls 102 are connected via the base 101 and the top plate 103 to form a frame or portal large enough for a person to enter. A target, which includes a person, stands on the base 101 while the portal screens the target, a process typically taking five to 30 seconds.

The portal may be either an open or closed design, although an open design with two parallel walls 102 as depicted in FIG. 1 is preferred for better throughput and for lower weight. The portal is then open on opposite sides so that people may line up on one side and each person, in turn, can enter the portal, wait until the screening process is complete, and exit the portal on the opposite side so that the next person can then enter the portal.

Figure 3:
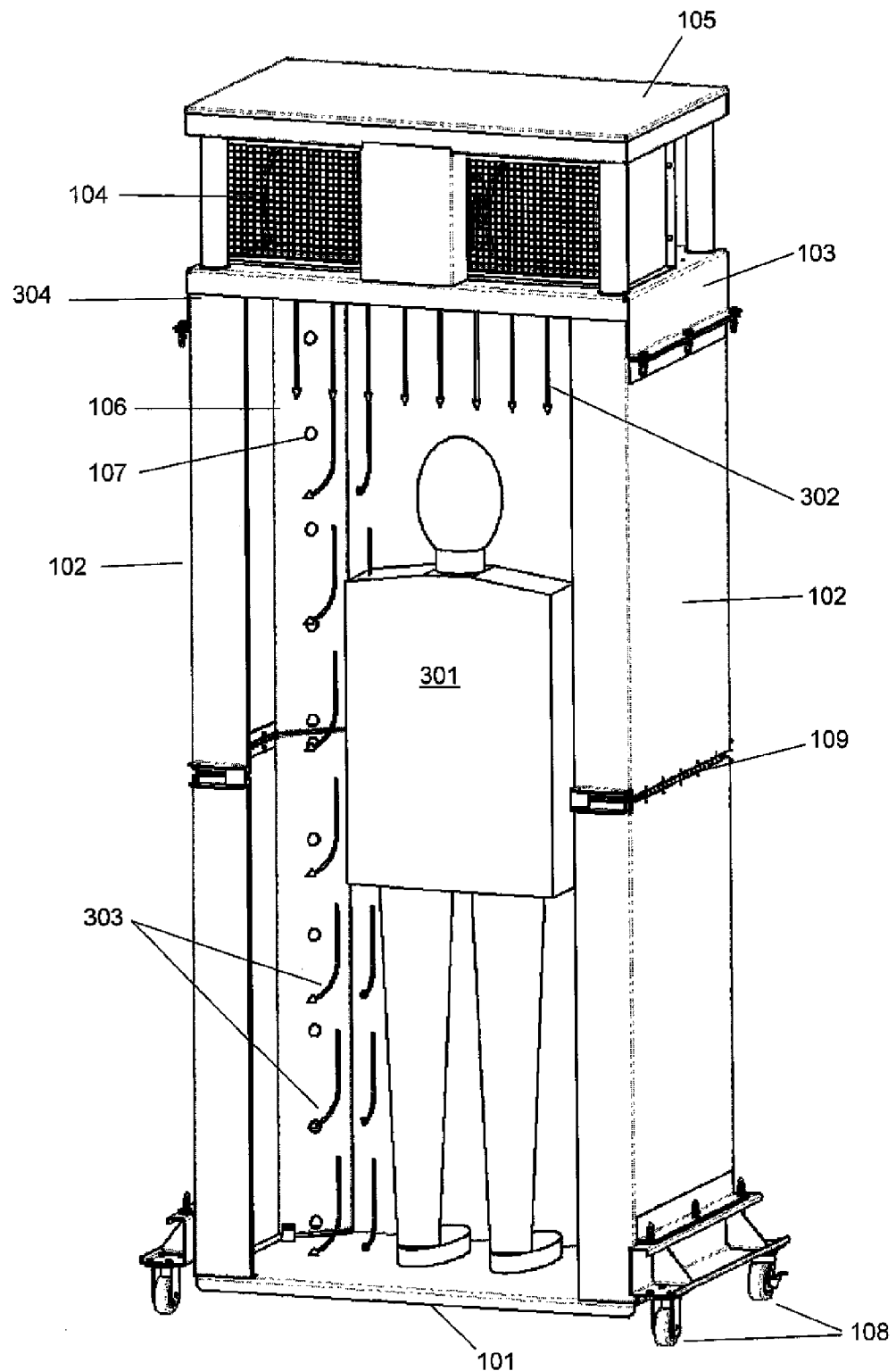
FIG. 3 is a perspective view of an embodiment of the invention showing a person inside the portal and depicting the air flow.

The invention relies on a blower, which may produce a laminar air flow as is routinely used in microelectronic fabrication facilities and hospitals. The blower may be referred to as a blower module 104. Any blower that can generate an air flow at a sufficient velocity may be employed. The blower module 104 is designed to blow air downward over the target at a velocity that is at least 10 meters per second. The air flow is depicted in FIG. 3 which shows a person 301 in the portal being showered with the air flow, with the air flow being depicted as arrows 302. The air flow dislodges and transports microscopic particles and vapor that may be on the person 301 or the person's clothing or other articles the person is carrying, with the assistance of gravity.

The blower module 104 takes in air through its portal air intake 203 and produces an air flow through its outflow manifold 201 which is located on the underside of the blower module 104 and which fits through a slot 202 in the top plate 103 so that the airflow is directed downward within the interior of the portal. The outflow manifold 201 may have multiple slots that may be adjustable to vary the air velocity impinging on the head and shoulders of a person 301 inside the portal and migrating downward though the person's clothing. The air flow may interact with the target to dislodge particles and vapor on or surrounding the target, such as microscopic particles of explosives on a person's clothes. Such particles and vapor are carried generally downward by the air flow.

The blower module 104 may also include a heater assembly. This could be mounted, for example, at the portal air intake 203 to heat incoming air above room temperature (room temperature being the temperature of the ambient air in the space in which the portal is located). It could alternately be mounted at the exit of the blower module 104 before the outflow manifold 201. The heater may be adjusted, for example, to heat the incoming air to a temperature of 35 to 45 degrees Celsius to provide warm air for the comfort of a person 301 in the portal, as well as to help in the out-gassing of materials from a person's clothes and belongings.

The walls 102 include air ducts 106 each having at least one duct air intake 107 in their surfaces facing the interior of the portal for receiving air from within the portal containing particles and vapors dislodged from the person 301 in the portal. In the depicted embodiment, each air duct 106 has 12 circular duct air intakes 107 spaced along the height of the portal at different heights above the base so that air may be sampled at many points along the body of a person 301 standing inside the portal. A duct air intake 107 has a relatively small open area that results in pneumatic communication between the interior region of the portal and the air duct 106 through which a vacuum unit, located in or in pneumatic communication with the air duct 106 can draw a sufficient sample of air into the air duct 106 from the interior of the portal. One or more duct air intakes 107 are employed to provide direct pneumatic communication between a range of heights within the portal. Preferably a plurality of at least two duct air intakes 107 are employed at different heights above the base to receive air directly from the interior region at those heights.

For example, each air duct 106 may have at least 6 small circular duct air intakes 107 spaced along the height of the portal, and more preferably at least 10, in a manner as is depicted in FIGS. 1-4. Alternatively one or more narrow slits could be used that provide direct sampling of the air in the interior of the portal at varying heights within the portal. In a preferred embodiment, the duct air intakes provide openings that can directly ingest air from within the portal at a plurality of intake points at different heights along the body of a person located in the interior region so that the highest intake point is at least three feet higher than the lowest intake point. The lowest intake point should be at most three feet above the feet of a person standing in the interior region. More preferably, the highest intake point is at least four feet higher than the lowest intake point and the lowest intake point is at most two feet above the feet of a person standing in the interior region The air ducts 106 may extend vertically from the bottom of the wall 102 to the top 304 of the wall 102, with the top of the air duct 106 being open for exhausting air to the space in which the portal is situated, or for connection to a recirculating manifold 105. The duct air intakes 107 may be covered with a coarse mesh to prevent the intake of large particles.

Because the duct air intakes 107 provide openings that can directly ingest air from within the portal at a plurality of heights, the portal may sample a small portion of the air entering the duct because samples of illicit materials at any point on a person's body will be readily drawn into an air duct 106 and be available to the detection module. As a result, clogging of the pre-concentrator assembly becomes much less likely than with prior art portals.

Figure 4:
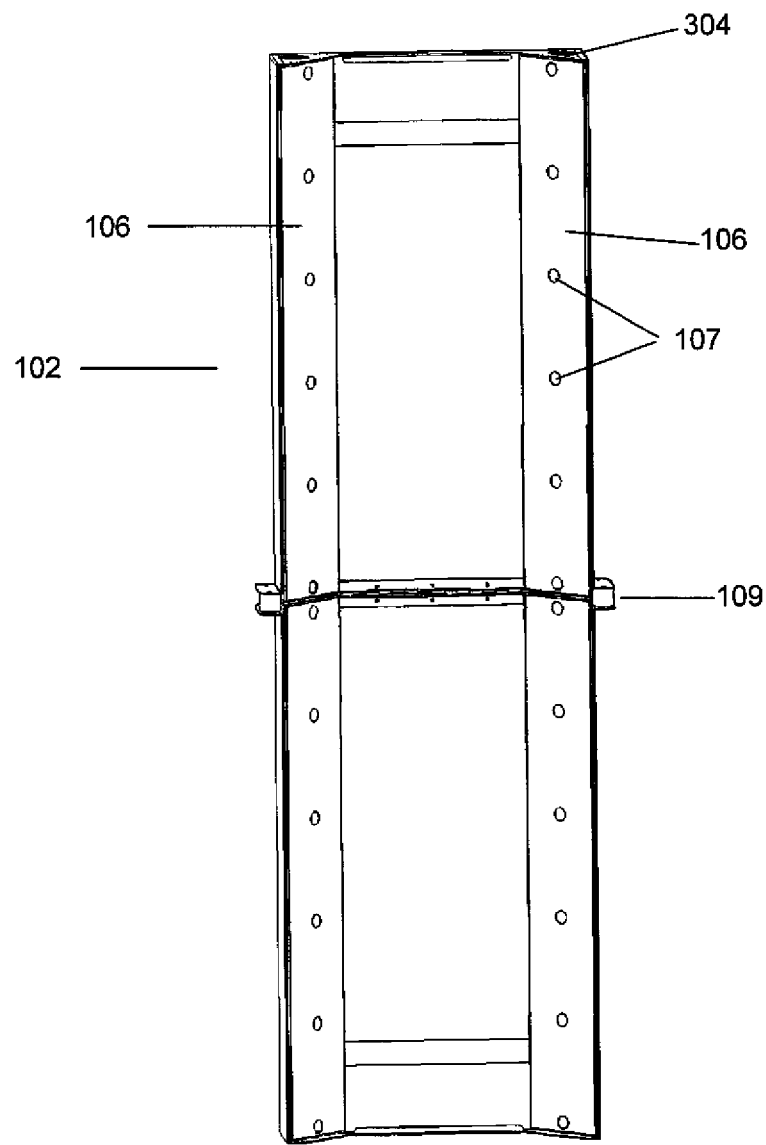
FIG. 4 is a side view of one wall of an embodiment of the invention.

A single wall is shown in FIG. 4. The embodiment shown in the figures includes two air ducts 106 per wall 102, each having a triangular cross-section. Each air duct 106 may have a vacuum unit, as part of a pneumatic system, located near the top 304 of the air duct 106 to draw air from the interior of the portal carrying particles and vapor through the duct air intakes 107 (as depicted by arrows 303 in FIG. 3), up towards the top 304 of the wall 102, and out the open top portion 304 of the air duct 106. In other embodiments the wall 102 may have a single air duct 106 with at least one duct air intake 107.

Figure 2:
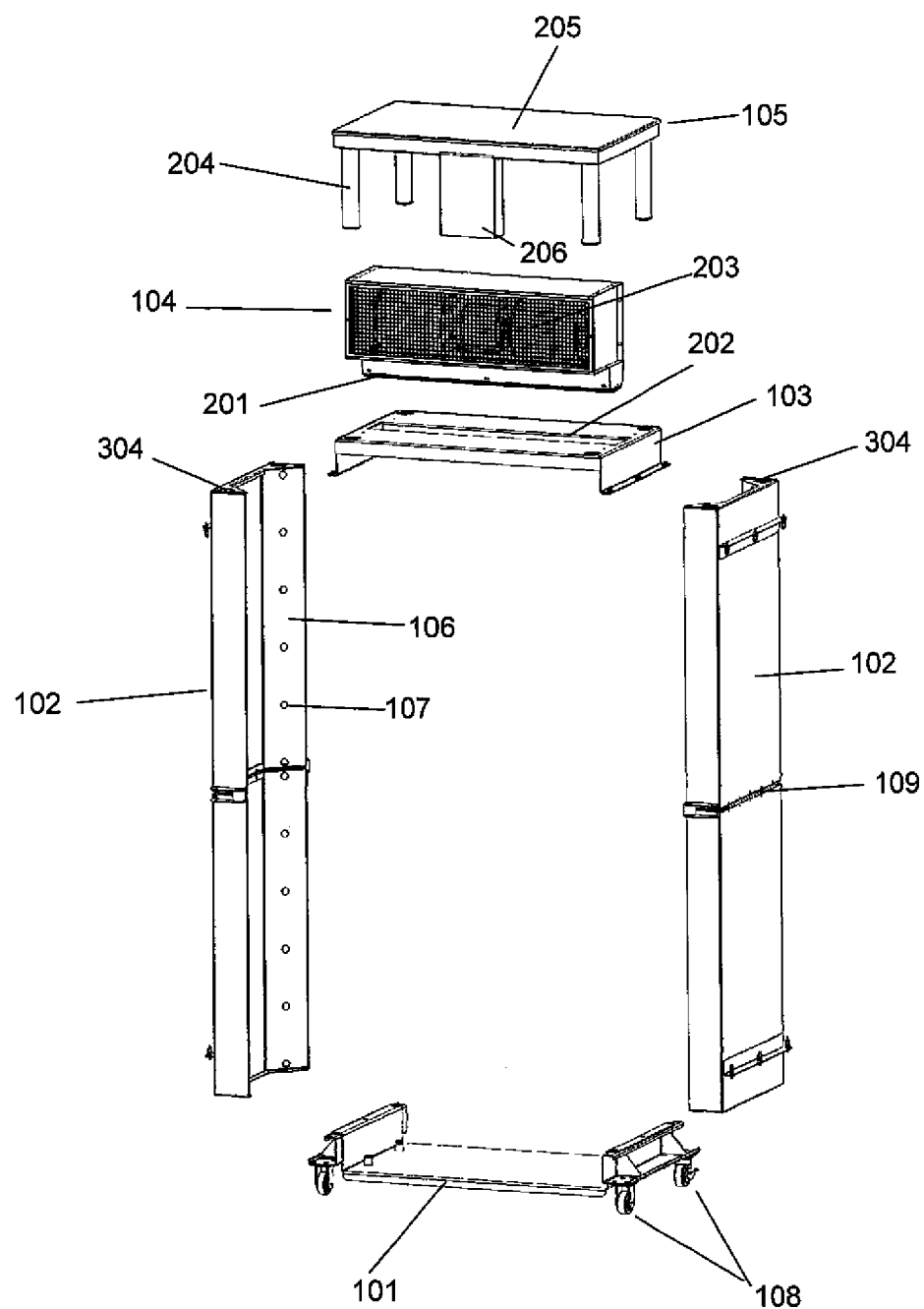
FIG. 2 is an exploded perspective view of an embodiment of the invention.

The recirculating manifold 105 has one uptake duct 204, as shown in FIG. 2, that connects pneumatically to the top 304 of each air duct 106 to receive the return air flow from the vacuum unit in the air duct 106. The air flows through the uptake duct 204 through the manifold housing 205, which provides an interior air passage, and is directed by a snorkel plate 206 back into the portal air intake 203 of the blower module 104 to recirculate the air containing particles and vapors dislodged from the person 301 in the portal so as to increase the concentration of such particles and vapors in the recirculated air. The manifold may be configurable, or may be detached, to prevent recirculation so that a single pass sampling of the target is performed. This may be advantageous, for example, during a decontamination procedure or when a large amount of an illicit material is present.

The air velocity inside the portal near the base 101 will be lower than at the top near the outflow manifold 201 of the blower module 104, typically being about 5-6 meters per second near the base 104. This can be increased by the inclusion of a fan in each wall 102 located near the bottom of the wall 102. These fans direct air towards the shoes of a person standing inside the portal to improve the ability of the portal to detect illicit material hidden in people's shoes.

Figure 5:
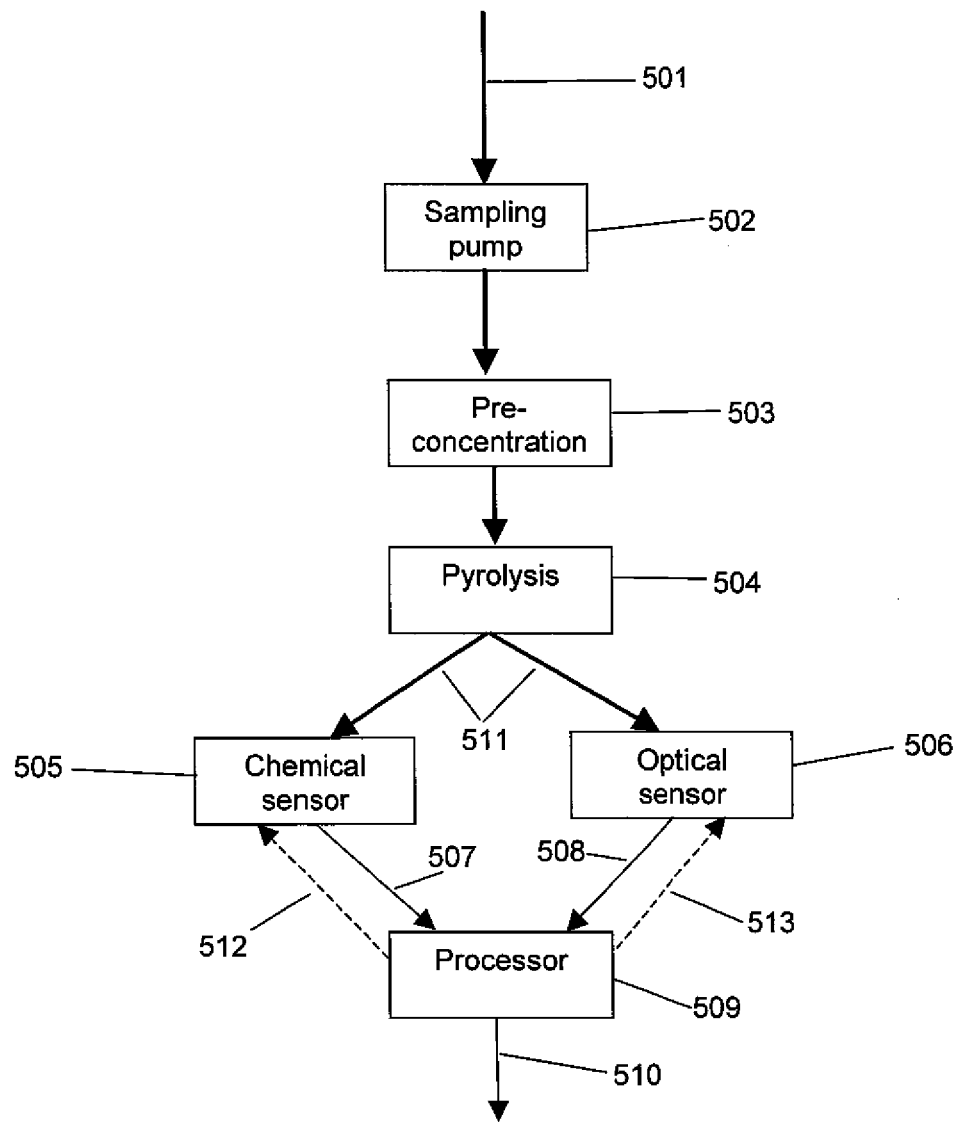
FIG. 5 is a flow diagram depicting the processing sequence performed by an embodiment of the detection module.

A detection module, as depicted schematically in FIG. 5, may be located on the exterior of each air duct 106, normally near the top 304 of the air duct 106, and sample duct air flow 501 via an air outlet in the air duct 106 (so that the air duct 106 and detection module are in pneumatic communication). This design allows the detection modules to be readily removed so that they can be easily replaced if a module fails. The depicted embodiment of the detection module includes a compact sampling pump 502 for withdrawing air carrying particles and vapor from the duct air flow 501 in the air duct 106. The sampling pump 502 directs the sampled air to a pre-concentrator unit that performs pre-concentration 503. A miniature pre-concentrator unit is preferred having a nano-platinum surface treated for concentration of vapors and trapping of microscopic particles. Such a miniature device may have a collection surface, or element, with an area of one square centimeter or less. The collection surface is coated with nanoscale platinum dendrites. Although such technology exists and has been used for other purposes, the current invention combines it with a novel mechanical and pneumatic design to produce a portal that has substantial advantages over prior art devices.

The collection surface captures microscopic particles and provides enrichment of collected vapors typically in the span of time of 5-10 seconds. The collection surface is then heated, under control of a microprocessor, typically to a temperature of 500 to 800 degrees Celsius for a duration of 1-2 seconds, to perform pyrolysis 504 of the sample by heating any vapors, fluid droplets and particulates to substantially vaporize them into their specific fragmentation products.

Some speciation may be obtained by employing multi-heated platinum elements at multiple temperatures. For example, four elements may be employed, each being heated to a different temperature (such as 500, 600, 700 and 800 degrees Celsius). Such an approach may be very useful in explosives detection as it results in a specific profile of the energetic material decomposition products that will be very different between different energetic materials, and which strongly distinguishes between energetic and non-energetic materials. Such an approach can significantly improve the sensitivity and specificity of the detection module.

The pyrolyzed materials 511 are detected by a chemical sensor 505 operating in reduction and oxidation modes that chemically analyzes the materials. The chemical sensor 505 is designed to react to chemical decomposition of certain illicit substances, such as explosives. Residues from explosive materials are abundant on surfaces after handling explosive materials, and are difficult to remove. Reduction mode is used for detection of explosives containing nitrogen and oxidation mode for non-nitrogen materials such as TATP. Volatile explosives, such as TATP, HMTD, EGDN, DMNB, NG, DNT and TNT are readily detected due to the fact that these explosives evaporate into the surrounding air even when concealed. Non-volatile explosives present as trace residue or particles adhering to clothes or surfaces such as pentaerythritol tetranitrate (PETN), cyclotrimethylenetrinitramine (RDX), octogen (HMX), 2,4,6,8,10,12-hexanitro-2,4,6,8,10,12-hexaazaisowurtzitane (HNIW), octanitrocubane, and others may also be detected by collecting dislodged particles.

The chemical sensor 505 may use any known chemical analysis technology and may be, for example, a mass spectrometer (stationary or portable), a chemiluminescence detector, a miniature axial ion mobility spectrometer (IMS), a field assymetric ion mobility spectrometry (FAIMS), a differential mobility spectrometer (DMS), a fast gas chromatography system interfaced to an electron-capture detector, or other electrochemical sensor.

This design allows for the detection of low nanogram levels for particles and concentrations of vapors of relatively low parts per billion.

An optical sensor 506 in the vicinity of the pyrolyzed materials 511 may capture specific emitted lights of highly reactive substances and provide a secondary detection capability. The optical sensor 506 may be optimized for specific frequencies indicative of the nature of pyrolyzed materials. When energetic materials are heated quickly they release electromagnetic radiation, such as infrared radiation, which can be picked up by the optical sensor. Furthermore, the material undergoes decomposition to specific fragment products, such as $NO/NO_2$ and other species, which may be detected by their light emission as a result of electronic excitation and relaxation to their electronic ground state.

A radiation sensor may also be employed to detect beta, gamma and alpha radioactivity emitted from radioactive materials on or with the target in the portal. The radiation sensor may use a variety of technologies, such as sodium iodide detectors, or technologies exploiting a Geiger-Mueller tube, halogen-quenched Geiger-Mueller tube, or similar technologies, depending on the desired application.

A processor 509 controls the sensors via control signals 512, 513 as well as the pre-concentration 503 and pyrolysis 504. The processor 509 receives analysis results 507, 508 from the chemical sensor 505 and optical sensor 506, as well as from the radiation sensor, if present. Based on this information, the processor 509 may determine whether an illicit substance is present and provide appropriate illicit substance information 510 to the operator of the portal. For example an alarm may be sounded and an indication of the identified illicit substances displayed on a screen. There may be a single processor 509 that handles all the detection modules, or each detection module may have its own processor that provides detection results to a central processor that then provides illicit substance information 510 to the operator. The portal may have a display that displays to the operator information regarding what the detection module is currently detecting or has detected. Information including, for example, which sensors have detected an illicit substance, what illicit substance or substances have been detected, the concentration or composition of the illicit substances, when applicable, and the date and time of the detection event may be logged for evidentiary purposes and displayed to the operator. The portal may also include a camera for recording a photograph of each target, or it may be programmed to record a photograph only if an illicit substance is detected.

Upon completion of the analysis, the target may be detained, confiscated or tagged if a positive indication of the presence of an illicit substance is produced. Tagged targets that are tolerant of microwaves or x-rays may also be subjected to further screening using imaging technologies that exploit these kinds of radiation.

Because of the use of multiple small detection modules that are connected to the air ducts 106 containing air sampled from a plurality of heights in the portal, the resulting portal is very compact and lightweight, and may be readily re-located within a facility through the incorporation of wheels 108 on the base 101. This allows one or two people to easily push the portal along a smooth surface such as a floor or ramp after it is disconnected from its power source. For example, the portal may be pushed against a metal detection are or radiation monitoring portal.

The invention could be manufactured with a single detection module in pneumatic communication with all air ducts 106, or with one detection module for each pair of air ducts 106 in each wall 102, but a design with one detection module per air duct 106 is preferred in order to obtain a compact and lightweight design.

The portal may be used indoors or outdoors as required with available AC power or an external generator. The pneumatic and electronic components operate from standard 120 VAC or 220 VAC power that is readily available. In a typical embodiment, each module is a separate assembly that can be removed and replaced as may be necessary and has its own processor (CPU) and electronics. A power supply may convert the input AC line power to 24 VDC for distribution to and use by the various modules.

The portal may be designed to operate in conditions of zero to fifty degrees Celsius and 10% to 95% relative humidity, non-condensing.

In the depicted embodiment, each wall 102 is comprised of two rigid portions, an upper portion and a lower portion, and has a folding joint 109, which may comprise one or more hinges and a releasable locking mechanism to lock the wall into a vertical position. The size of the two portions is typically approximately equal so that the height, or spatial extent, of the folded wall 102 is minimized. The separated components, including the folded wall 102, may then be easily transported.

Figure 6:
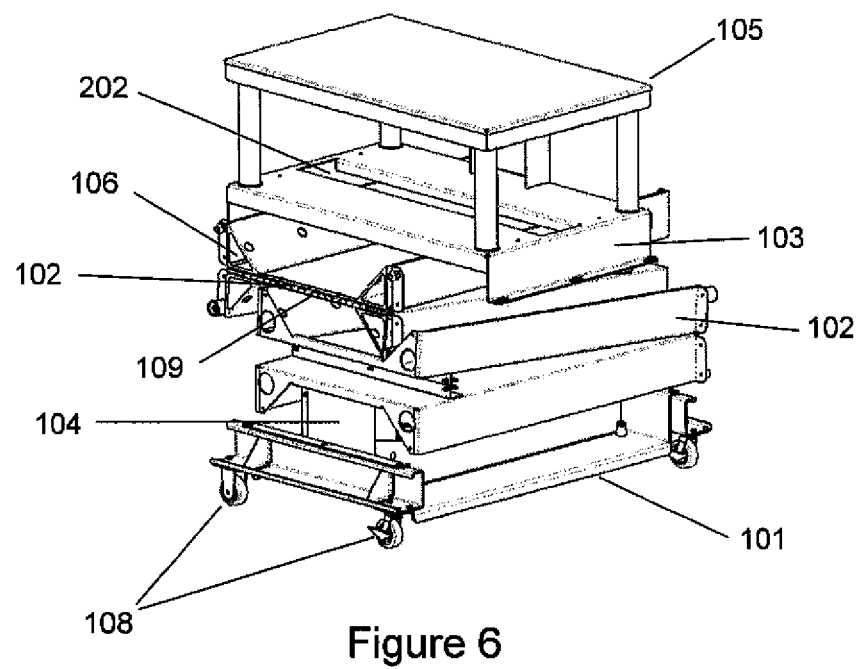
FIG. 6 is a perspective view of an embodiment of the invention in a disassembled and folded state.

The portal is designed and fabricated so that it can be readily disassembled to separate the components, which are depicted individually in FIG. 2, and transported. The portal may be transported to locations where it is needed for screening people and their belongings, for example, at a sporting event, a large gathering, a conference, or a government meeting or summit. After the manifold 205 is removed, the blower module 104 may then be removed, followed by the top plate 103 and the walls 102. After the walls 102 are removed they may then be folded by releasing the locking mechanism to bring the upper and lower portions together by rotating them around the folding joint 109. FIG. 6 shows the disassembled and folded portal where the blower module 104 has been first placed on the base 101, the folded walls 102 being placed on top of the blower module 104, and then the top plate 103 and recirculating manifold 105 being placed on top of the folded walls 102.

The resulting disassembled portal can then be placed into a space having a relatively small volume, such as the back of a vehicle, and easily transported to another site where it can quickly be reassembled and used to screen people or other targets. When the portal is disassembled and the walls folded, the disassembled portal may fit in a space that is less than 1.5 cubic meters in volume, or, in a preferred embodiment, less than 1.0 cubic meters.

A typical embodiment of the portal may weigh less than 200 kilograms or, in a preferred embodiment, 100-150 kilograms. Thin aluminum panels may be used to construct the walls in order to keep the weight relatively low and thereby facilitate easy movement and transportation of the portal.

The portal can be dissembled or reassembled easily by two people using hand tools in less than an hour. Hand tools include any tools, such as a screwdriver, that may be carried by one person and operated by one or two people, and which may or may not be powered.

While the invention has been described for use in screening people standing in the interior region, the invention is not limited in this manner. Embodiments of varying sizes could be constructed for purposes of screening various items, such as cargo. Such items could, for example, be moved though the interior region on a conveyer belt that passes through the interior region and stops, for example for five to 30 seconds, when each item on the belt is in the interior region to allow it to be screened.

It will be appreciated by skilled persons that the processor 509 described herein may comprise one or more computer processors which are preferably programmable by software to perform the functions as described herein. The processor(s) may alternately be purpose-built hardware designed to perform only the functions required to implement the invention. Where multiple processors are employed they may be connected by wires using standard protocols or they may communicate wirelessly and be physically remote from each other and/or the sensors.

The foregoing description illustrates only certain preferred embodiments of the invention. The invention is not limited to the foregoing examples. That is, persons skilled in the art will appreciate and understand that modifications and variations are, or will be, possible to utilize and carry out the teachings of the invention described herein. Accordingly, all suitable modifications, variations and equivalents may be resorted to, and such modifications, variations and equivalents are intended to fall within the scope of the invention as described and within the scope of the claims.

What is claimed is:

1. A portal for screening a target that includes a person, the portal comprising:
    a. a frame defining an interior region for accommodating the target, the frame having at least one vertical portion being an air duct for receiving air from the interior region, each duct being a vertical conduit extending substantially from the bottom of the frame to the top of the frame and having at least two openings at surfaces of the frame adapted to receive air carrying particles and vapor flowing downward along the surfaces at at least two different heights along the frame so the air received from each of the two heights is combined into a single flow of air through the duct, the air duct extending above the person located in the interior region;
    b. a blower module positioned above the interior region for directing a flow of air downward at the target in the interior region to dislodge particles and vapor on or surrounding the target, wherein the air flow carries the dislodged particles and vapor away from the target and to the openings; and
    c. a detection module in pneumatic communication with each air duct for sampling and processing air in the air ducts, the detection module comprising a pre-concentrator module for collecting and pre-concentrating the particles and vapor from the air, and a chemical sensor for detecting illicit substances by chemically analyzing the pre-concentrated particles and vapor.

2. The portal of claim 1 wherein the interior region is at least six feet high and the highest opening is at least three feet higher than the lowest opening.

3. The portal of claim 2 wherein the lowest opening is at most three feet above the feet of a person standing in the interior region.

4. The portal of claim 3 wherein the highest opening is at least four feet higher than the lowest opening and the lowest opening is at most two feet above the feet of a person standing in the interior region.

5. The portal of claim 2 wherein each air duct has at least six duct air openings for receiving air from six different heights.

6. The portal of claim 1 wherein the pre-concentrator module pyrolyzes particles and vapor.

7. The portal of claim 1 wherein the frame comprises two walls, each wall having at least one air duct.

8. The portal of claim 7 wherein each wall has two air ducts extending to the top of the walls and the portal further comprises a pneumatic system for drawing the air carrying particles and vapor through the air ducts towards the tops of the walls, wherein a separate detection module is in pneumatic communication with each air duct, and the portal further comprises a manifold for receiving air carrying particles and vapor from the air ducts and directing the air to the blower module for recirculation of the air.

9. The portal of claim 8 wherein the portal can be configured to prevent recirculation of the air.

10. The portal of claim 8 further comprising a fan in each wall located near the bottom of the wall.

11. The portal of claim 7 wherein each wall comprises at least two rigid portions, the portions being foldably attached to each other for folding the wall to reduce its spatial extent.

12. The portal of claim 11 wherein the portal may be disassembled and the walls folded so that the disassembled portal fits in a space that is less than one cubic meter in volume.

13. The portal of claim 1 wherein the detection module further comprises an optical sensor.

14. The portal of claim 1 wherein the detection module further comprises a radiation sensor for detecting beta, gamma and alpha radioactivity.

15. The portal of claim 1 wherein the portal further comprises a processor for receiving analysis results from the detection module and generating illicit substance information.

16. The portal of claim 1 wherein the pre-concentrator module is a miniature pre-concentrator comprising a surface coated with platinum nano-dendrites.

17. The portal of claim 6 wherein the pre-concentrator module comprises more than one collection surface and wherein the pyrolysis is performed by heating the collection surfaces to different temperatures.

18. The portal of claim 17 wherein the pre-concentrator module comprises four collection surfaces.

19. The portal of claim 1 wherein the chemical sensor is selected from the group consisting of: an ion mobility spectrometer, a differential mobility spectrometer, a mass analyzer system, and a fast gas chromatography system interfaced to an electron-capture detector.

20. The portal of claim 1 wherein the portal further comprises wheels for moving the portal along a surface.

21. The portal of claim 1 wherein the interior region comprises a perimeter adjacent to the frame and each opening is adapted to allow downward airflow at the perimeter to enter the opening.

22. The portal of claim 1 wherein the frame does not include an obstruction that would prevent downward airflow at the surfaces from entering the openings.

23. The portal of claim 1 wherein each opening has an opening top and an opening bottom, and the frame does not include obstructions to airflow extending horizontally from the surfaces at the opening tops.

24. The portal of claim 1 wherein the frame does not include elongate hollow conduits enclosing each opening and extending from each of the openings to locations at the interior region.

* * * * *